US008815787B2

(12) United States Patent
Ikegaki et al.

(10) Patent No.: US 8,815,787 B2
(45) Date of Patent: Aug. 26, 2014

(54) SKIN CLEANSING AGENT

(75) Inventors: Shinichi Ikegaki, Sumida-ku (JP); Kenji Kaneda, Sumida-ku (JP)

(73) Assignee: Kao Corporation, Tokyo (JP)

( * ) Notice: Subject to any disclaimer, the term of this patent is extended or adjusted under 35 U.S.C. 154(b) by 120 days.

(21) Appl. No.: 13/512,049

(22) PCT Filed: Dec. 8, 2010

(86) PCT No.: PCT/JP2010/072021
§ 371 (c)(1),
(2), (4) Date: May 25, 2012

(87) PCT Pub. No.: WO2011/071079
PCT Pub. Date: Jun. 16, 2011

(65) Prior Publication Data
US 2012/0277137 A1 Nov. 1, 2012

(30) Foreign Application Priority Data

Dec. 8, 2009 (JP) .................................. 2009-278657

(51) Int. Cl.
| | |
|---|---|
| C11D 1/04 | (2006.01) |
| C11D 1/722 | (2006.01) |
| C11D 3/12 | (2006.01) |
| A61Q 19/10 | (2006.01) |
| C11D 1/72 | (2006.01) |
| C11D 1/83 | (2006.01) |
| A61Q 19/02 | (2006.01) |
| A61Q 5/02 | (2006.01) |
| A61K 8/36 | (2006.01) |
| A61K 8/86 | (2006.01) |

(52) U.S. Cl.
CPC ........ *A61Q 19/10* (2013.01); *C11D 1/72* (2013.01); *C11D 3/1253* (2013.01); *C11D 3/12* (2013.01); *C11D 1/83* (2013.01); *C11D 3/1266* (2013.01); *A61Q 19/02* (2013.01); *A61Q 5/02* (2013.01); *C11D 3/124* (2013.01); *C11D 1/04* (2013.01); *A61K 8/361* (2013.01); *A61K 8/86* (2013.01); *A61K 2800/28* (2013.01); *A61K 2800/412* (2013.01)
USPC ........... 510/119; 510/130; 510/136; 510/137; 510/138; 510/477; 510/488; 510/506

(58) Field of Classification Search
CPC .............. C11D 1/04; C11D 1/72; C11D 1/83; C11D 3/12; C11D 3/124; C11D 3/1253; C11D 3/1266; A61Q 5/02; A61Q 19/02; A61K 8/0241; A61K 8/04
USPC ......... 510/119, 130, 136, 137, 138, 477, 488, 510/506; 424/70.11, 70.31
See application file for complete search history.

(56) References Cited

U.S. PATENT DOCUMENTS

| | | | | |
|---|---|---|---|---|
| 5,525,263 | A * | 6/1996 | Bimczok et al. ............... | 510/128 |
| 6,194,364 | B1 * | 2/2001 | Glenn, Jr. ....................... | 510/130 |
| 6,287,577 | B1 * | 9/2001 | Beerse et al. .................. | 424/401 |
| 6,287,583 | B1 * | 9/2001 | Warren et al. .................. | 424/404 |
| 6,495,498 | B2 * | 12/2002 | Niemiec et al. ............... | 510/122 |
| 7,915,214 | B2 * | 3/2011 | SenGupta et al. ............ | 510/417 |
| 2001/0029243 | A1 | 10/2001 | Meiwa et al. | |
| 2002/0055446 | A1 * | 5/2002 | Perron et al. ................... | 510/119 |
| 2002/0173435 | A1 * | 11/2002 | Librizzi ........................ | 510/130 |
| 2005/0031573 | A1 * | 2/2005 | Cho et al. ......................... | 424/74 |
| 2006/0116305 | A1 * | 6/2006 | Yamato et al. ................. | 510/124 |
| 2006/0142174 | A1 * | 6/2006 | Fukuda et al. ................. | 510/510 |
| 2007/0289613 | A1 * | 12/2007 | Geary et al. ..................... | 134/34 |
| 2008/0070966 | A1 * | 3/2008 | Elder et al. ..................... | 514/385 |
| 2008/0242581 | A1 * | 10/2008 | Murphy et al. ............... | 510/414 |

FOREIGN PATENT DOCUMENTS

| | | |
|---|---|---|
| JP | 4 18494 | 1/1992 |
| JP | 4-18494 A | 1/1992 |
| JP | 8 3030 | 1/1996 |
| JP | 9 12444 | 1/1997 |
| JP | 9-12444 A | 1/1997 |
| JP | 2000 351993 | 12/2000 |
| JP | 2000-351993 A | 12/2000 |
| JP | 2002 346362 | 12/2002 |
| JP | 2002-346362 A | 12/2002 |
| JP | 2003 212753 | 7/2003 |
| JP | 2005 336068 | 12/2005 |
| JP | 2005-336068 A | 12/2005 |
| JP | 2006 160673 | 6/2006 |
| JP | 2011 79743 | 4/2011 |

OTHER PUBLICATIONS

International Search Report Issued Mar. 1, 2011 in PCT/JP10/72021 Filed Dec. 8, 2010.
Combined Chinese Office Action and Search Report issued Jan. 17, 2013, in Chinese Patent Application No. 201080055765.5 with English translation of category of cited documents.

* cited by examiner

*Primary Examiner* — Gregory R Delcotto
(74) *Attorney, Agent, or Firm* — Oblon, Spivak, McClelland, Maier & Neustadt, L.L.P.

(57) ABSTRACT

Provided is a skin cleanser, including the following components (A) to (D): (A) 1 to 30% by weight of a higher fatty acid or a salt thereof; (B) 0.5 to 10% by weight of a polyoxyethylene alkyl ether carboxylic acid or a salt thereof; (C) 0.1 to 10% by weight of an amphiphilic substance having an IOB of 0.25 to 1.2; and (D) 1 to 25% by weight of a water-insoluble particle having an average particle diameter of 50 to 500 μm, in which a weight ratio between the components (A) and (B) "(A)/(B)" is 1/2 to 10/1.

19 Claims, No Drawings

SKIN CLEANSING AGENT

FIELD OF THE INVENTION

The present invention relates to a skin cleanser.

BACKGROUND OF THE INVENTION

As means for enhancing a cleansing effect and a cleansing feeling during cleansing, there is known a scrub cleanser containing particles. When the scrub cleanser is used in a foamed state, its particles penetrate into small unevenness in a skin, such as pores and skin furrows, and remove sebum and dirt present in the pores and skin furrows as well as allowing a user to have a feeling of particle. Thus, the particles in the cleanser can provide the user satisfactory feeling of dirt removal.

For example, Patent Document 1 describes that cleansing compositions excellent in foamability are obtained by combining a fatty acid having a specific composition and a salt thereof and water-insoluble particles in the former document. and Patent Document 2 describes that cleansing compositions excellent in foamability are obtained by combining a higher fatty acid salt, a specific amino acid-based surfactant, and water-insoluble solid powder in the latter document. However, those cleansing compositions each have a problem in that the composition has creamy foam quality when being foamed, and hence the foam envelopes the particles to impair a feeling of the particles during cleansing, with the result that the cleansing effect and cleansing feeling derived from the particles are not provided. On the other hand, when particles having larger particle diameters are used in order to provide moderate particle feeling even during cleansing, there arises a problem in that the feeling of particle is so intense at the start of cleansing as to give the user an uncomfortable feeling.

Patent Document 3 describes a scrubbing cleansing composition containing sodium hydrogen carbonate particles having a specific particle size distribution and a fatty acid salt. However, as the fatty acid salt is used within a range of the controlled particle diameters, the cleansing composition also has a problem in that foam envelopes the particles during cleansing to thereby impair the feeling of particle.

It should be noted that none of Patent Documents 1, 2, and 3 has any description about controlling sustainability of the particles by modifying foam quality in an actual use.

As described above, various particle-containing cleansers have been studied, but none of the cleansers has provided a sustained moderate feeling of particle because foaming during its use causes the particles to be enveloped in the foam.

PRIOR ART DOCUMENT

Patent Document

[Patent Document 1] JP-A-2006-160673
[Patent Document 2] JP-A-08-3030
[Patent Document 3] JP-A-2003-212753

SUMMARY OF THE INVENTION

The present invention provides a skin cleanser, including the following components (A) to (D):
(A) 1 to 30% by weight of a higher fatty acid or a salt thereof;
(B) 0.5 to 10% by weight of a polyoxyethylene alkyl ether carboxylic acid or a salt thereof;
(C) 0.1 to 10% by weight of an amphiphilic substance having an IOB of 0.25 to 1.2; and
(D) 1 to 25% by weight of a water-insoluble particle having an average particle diameter of 50 to 500 μm,
in which a weight ratio between the components (A) and (B) "(A)/(B)" is 1/2 to 10/1.

EFFECTS OF THE INVENTION

The skin cleanser of the present invention has a basic performance as a cleanser, i.e. foaming property and gentleness to the skin. Thus the skin cleanser of the present invention can, during its use, give the user an enhanced cleansing feeling and a reliable cleansing effect with such foam quality that allows the user to have moderate feeling of the particle sustainably.

EMBODIMENTS FOR CARRYING OUT THE INVENTION

The present invention relates to a skin cleanser, which can give a user enhanced cleansing feeling and a reliable cleansing effect by sustaining a feeling of particle at a moderate intensity even when the cleanser foams during cleansing through control of physical properties of foam during its use.

The inventors of the present invention have found that a skin cleanser that has solved the problems is obtained by using water-insoluble particles (scrub) in combination with a higher fatty acid salt, a polyoxyethylene alkyl ether carboxylic acid or a salt thereof, and a specific amphiphilic substance.

A higher fatty acid or a salt thereof as a component (A) to be used in the present invention is preferably represented by the following formula (1).

$$R^1\text{—COOX} \qquad (1)$$

(In the formula, $R^1$ represents an alkyl group having 11 to 23 carbon atoms, and X represents a hydrogen atom, an alkali metal, ammonium, or an organic ammonium.)

In the formula (1), $R^1$ preferably represents a linear alkyl group having 11 to 16 carbon atoms. Further, examples of X include: alkali metals such as sodium and potassium; ammonium; alkanolamines such as monoethanolamine, diethanolamine, and triethanolamine ; and cations derived from basic amino acids such as arginine and lysine.

Exemplary component (A) includes lauric acid, myristic acid, palmitic acid, stearic acid, arachic acid, behenic acid, lignoceric acid, and salts thereof, and preferred are lauric acid, myristic acid, palmitic acid, and salts thereof. Of those, potassium salts of lauric acid, myristic acid, and palmitic acid are more preferred.

One or two or more types of the higher fatty acids or salts thereof as the component (A) may be used, and a content thereof is 1 to 30% by weight, preferably 1 to 25% by weight, and more preferably 2 to 20% by weight based on the total weight of the composition. When the content falls within the range, quick foaming and satisfactory rinsability may be provided. It should be noted that the higher fatty acid or the salt thereof as the component (A) is preferably free of branched and unsaturated fatty acids.

A component (B) to be used in the present invention is a polyoxyethylene alkyl ether carboxylic acid or a salt thereof, and is preferably represented by the following formula (2).

$$R^2\text{—O(CH}_2\text{—CH}_2\text{O)m-CH}_2\text{COOM} \qquad (2)$$

(In the formula, $R^2$ represents an alkyl group or alkenyl group having 10 to 18 carbon atoms, m represents a number of 0.5 to 10 on average, and M represents a hydrogen atom or an alkali metal.)

In the formula (2), $R^2$ preferably represents an alkyl group having 12 to 16 carbon atoms. In addition, the average number of moles of ethylene oxide added represented by m, which is 0.5 to 10, is preferably 1 to 6.

The alkali metal represented by M, is for example, sodium or potassium, and an alkali metal hydroxide such as sodium hydroxide or potassium hydroxide may be used in blending. The alkali metal hydroxide is preferably potassium hydroxide with a view to use as a water-based cleanser.

One or two or more types of the component (B) may be used, and a content thereof in terms of polyoxyethylene alkyl ether carboxylic acid is 0.5 to 10% by weight, preferably 1 to 8% by weight, and more preferably 2 to 7% by weight based on the total weight of the composition. When the content falls within the range, slippery foam and refreshing feeling without slimy feeling at the time of rinsing can both be achieved.

In the present invention, the combination of the components (A) and (B) produces a soft foam film, and hence a moderate feeling of particle of scrub in an early period of use (early period of foaming) is easily obtained.

A weight ratio between the components (A) and (B) "(A)/(B)" is 1/2 to 10/1, preferably 1/2 to 7/1. When the ratio is less than 1/2, foam quality and rinsability deteriorate. As a result, although a scrub feeling is obtained, slimy feeling arises at the time of rinsing to impair the refreshing feeling of cleansing. Meanwhile, when the ratio is more than 10/1, a fine and dense foam is produced, and hence the foam covers up the particles. As a result, a feeling of particle and a cleansing feeling during use are hardly obtained.

A component (C) is an amphiphilic substance having an IOB of 0.25 to 1.2. The IOB of the component (C) is preferably 0.26 to 1.1, and more preferably 0.43 to 0.9.

Here, the "IOB" refers to a ratio between an inorganic value and an organic value (inorganic organic balance) determined based on an organic conceptual diagram (Atsushi Fujita, Prediction of Organic Compounds and Organic Conceptual Diagram, Journal of Japanese Chemistry Vol. 11, No. 10 (1957) 719-725), and is determined by the following equation.

$$IOB \text{ value} = \frac{\text{Inorganic value}}{\text{Organic value}}$$

More specifically, examples of the component (C) include: a polyoxyethylene alkyl ether such as a POE (3.3) monoalkyl (C12 to 14) ether (IOB=0.89), polyoxyethylene octyl dodecyl ether (5E.O.) (IOB=0.81), polyoxyethylene octyl dodecyl ether (10E.O.) (IOB=1.08), polyoxyethylene isostearyl ether (5E.O.) (IOB=0.86), and polyoxyethylene isostearyl ether (10E.O.) (IOB=1.13); a polyoxyethylene sorbitan fatty acid ester such as polyoxyethylene sorbitan monostearate (6E.O.) (IOB=1.15); a polyoxyethylene hydrogenated castor oil such as a polyoxyethylene hydrogenated castor oil (7E.O.) (IOB=0.71) and a polyoxyethylene hydrogenated castor oil (20E.O.) (IOB=1.02); a (di)glycerin monofatty acid ester such as glycerin monostearic acid ester (IOB=0.59) and glycerin monocaprylic acid ester (IOB3=1.18); a nonionic surfactant including a (di)glycerin monoalkyl ether such as glycerin mono-2-ethylhexyl ether (IOB=1.05); a branched fatty acid such as isostearic acid (IOB=0.43); and a branched higher alcohol such as 2-octyldodecanol (IOB=0.26) and isostearyl alcohol (IOB=0.29).

Of those, a polyoxyethylene alkyl ether, a polyoxyethylene sorbitan fatty acid ester, a polyoxyethylene hydrogenated castor oil, and a (di)glycerin monoalkyl ether are preferred.

Further, the component (C) preferably has a molecular weight of 100 to 550 because such molecular weight is about the same as those of the component (A) and the component (B), and molecules of the component (C) are estimated to be able to align in a gas-liquid interface in the same manner as molecules of the component (A) and molecules of the component (B).

In addition, the component (C) more preferably has a branched alkyl chain or multiple chain structure or a structure of a secondary alcohol having an ethylene oxide chain because such component (C) provides a large effect on enhancing fluidity through disturbance of the alignment of the molecules of the component (A) and the component (B) in a foam film, and hence can prevent the foam from becoming fine through massage.

Exemplary component (C) includes POE (5) isostearyl ether (IOB=0.86, molecular weight: 490), POE (5) octyl dodecyl ether (IOB=0.81, molecular weight: 518), isostearic acid (IOB=0.43, molecular weight: 284), 2-octyldodecanol (IOB=0.26, molecular weight: 298), POE (3.3) monoalkyl (C12 to 14) ether (IOB=0.89, molecular weight: 345), and glycerin mono-2-ethylhexyl ether (IOB=1.05, molecular weight: 204).

One or two or more types of the component (C) may be used, and a content thereof is 0.1 to 10% by weight, preferably 0.2 to 8% by weight, and more preferably 0.3 to 5% by weight based on the total weight of the composition. When the content falls within the range, the cleanser may be adjusted so as not to produce foam having a high foam density (relatively large foam containing a large amount of air, which hardly becomes creamy) even when rubbed to foam.

In a general cleanser, it is considered that the cleanser preferably produces fine and dense foam in a large amount. On the other hand, as the skin cleanser of the present invention has a purpose of sustaining a feeling of particle of the water-insoluble particle (D), the feeling of particle cannot be sustained with the fine and dense foam. In the present invention, a soft foam film is formed with the component (A) and the component (B), followed by further subjecting to modification with the component (C). Thus, the feeling of particle can be fully felt and sustained as well. It is estimated that the foam film is formed by molecules of the component (A) and molecules of the component (B) aligned in a gas-liquid interface, and that molecules of the component (C) exist as being interposed between the molecules of the component (A) and the molecules of the component (B) and can modify the texture of the foam film. Therefore, while satisfactorily foaming, the cleanser produces foam having a small foam density (relatively large foam containing a large amount of air), and hence the feeling of particle can be sustained.

When the component (C) is contained so that a weight ratio among the components (A), (B), and (C) "((A)+(B))/(C)" is preferably 2/1 to 30/1, and more preferably 2.5/1 to 10/1, a preferred foam density can be maintained.

A component (D) to be used in the present invention is a water-insoluble particle having an average particle diameter of 50 to 500 μm.

Exemplary component (D) includes inorganic powders of titanium dioxide, talc, kaolin, bentonite, sodium chloride, silica, mica titanium, and the like, a silicone powder, a silk powder, a hemp powder, and organic powders of saccharide such as cellulose or a derivative thereof and synthetic polymers such as polyethylene, polypropylene, polyethylene oxide, an ethylene-acrylic acid copolymer, polystyrene, nylon, and an acrylic resin.

Further, there may also be used a granulated powder obtained by using the water-insoluble particles as primary particles and binding together a plurality of powders with a binder. As the binder, there maybe used, for example: a synthetic product such as a polyvinyl alcohol and/or a derivative thereof, a poly(meth)acrylic acid alkali salt, an alkali salt of a (meth)acrylic acid ester copolymer, an alkali salt of an acrylic acid/maleic acid copolymer, and polyvinylpyrrolidone; semi-synthetic products such as methylcellulose, ethylcellulose, carboxymethylcellulose, hydroxyalkylcellulose, and a starch derivative; and natural polymers such as starch, seaweeds, plant mucus, and protein.

Of those water-insoluble particles, a water-insoluble granulated powder is preferred.

Of those, it may be more preferred to use a polyvinyl alcohol and/or a derivative thereof as the binder because rinsing water at the time of rinsing allows the granulated powder to easily disintegrate, and hence rinsability is enhanced. Even more preferred example of the granulated powder is a granulated powder obtained by granulating a primary particle of cellulose having an average particle diameter of 1 to 70 µm with maleic acid-modified polyvinyl alcohol as the binder so as to have an average particle diameter of 50 to 500 µm. The powder is more preferred because its particles are allowed to easily disintegrate by rinsing water or tear in the process of cleansing and rinsing, and hence cause little damage or itchiness to the skin and have extremely satisfactory rinsability.

The water-insoluble particle as the component (D) has an average particle diameter (measured with a laser diffraction/scattering particle size distribution measuring apparatus LA-910 (manufactured by Horiba, Ltd.), a median diameter was used as the average particle diameter) of 50 to 500 µm. When the average particle diameter is less than 50 µm, the use of the cleanser in a foamed state hardly gives feeling of the particles and also provides decreased cleansing power for pores and skin furrows. When the average particle diameter is more than 500 µm, uncomfortable feeling to the skin may arise during the use. In order to achieve a moderate feeling of particle, a cleansing effect and cleansing feeling, the average particle diameter is preferably 60 to 400 µm.

Further, large particles (each having an average particle diameter of 240 to 500 µm, preferably 250 to 350 µm) and small particles (each having an average particle diameter of 50 to 130 µm, preferably 80 to 120 µm) are preferably used in combination. In addition, a weight ratio of the large particles (each having an average particle diameter of 240 to 500 µm, preferably 250 to 350 µm) to the small particles (each having an average particle diameter of 50 to 130 µm, preferably 80 to 120 µm) is preferably 1/2 to 1/12, and more preferably 1/3 to 1/10 because the cleansing effect is more enhanced.

One or two or more types of the component (D) may be used, and a content thereof is 1 to 25% by weight, preferably 2 to 15% by weight based on the total weight of the composition.

The skin cleanser of the present invention may further contain (E) a polymeric thickener to improve dispersion stability of the particles and convenience in use.

Exemplary polymeric thickener is preferably an acrylic acid/alkyl methacrylate copolymer, and examples thereof include Carbopol ETD-2020, Carbopol 1342, Carbopol 1382, Pemulen TR-1, and Pemulen TR-2 (all of which are manufactured by NOVEON).

One or two or more types of the polymeric thickener as the component (E) may be used, and a content thereof is preferably 0.05 to 1.5% by weight, 0.2 to 1.2% by weight, and more preferably 0.4 to 0.9% by weight based on the total weight of the composition. When the content falls within the range, the cleanser is easily applied from a container to one's hand and easily spread by being extremely easily dissolved when mixed with water in use.

In the present invention, water accounts for a balance of the composition, in addition to the components (A) to (E), and a content thereof is preferably 30 to 90% by weight, and more preferably 50 to 80% by weight based on the total weight of the composition.

Further, when the skin cleanser of the present invention is used in combination with an amphoteric surfactant such as a carboxylic acid-type amphoteric surfactant, a sulfonic acid-type amphoteric surfactant, or a phosphate-type amphoteric surfactant, the stability (prevention of suspension and precipitation) of the component (D) after being stored at low temperature can be secured.

In the skin cleanser of the present invention, it is more preferred that the preferred ranges of the respective components be used in combination.

It is preferred that the skin cleanser of the present invention contain:
(A) 1 to 30% by weight of a higher fatty acid or a salt thereof;
(B) 0.5 to 10% by weight of a polyoxyethylene alkyl ether carboxylic acid or a salt thereof;
(C) 0.1 to 10% by weight of an amphiphilic substance having an IOB of 0.25 to 1.2; and
(D) 1 to 25% by weight of a water-insoluble particle having an average particle diameter of 50 to 500 µm,
in which:
the weight ratio between the components (A) and (B) "(A)/(B)" be 1/2 to 10/1; and
the weight ratio among the components (A), (B), and (C) "((A)+(B))/(C)" be 2/1 to 30/1.

In a further preferred embodiment, the skin cleanser according to the present invention includes:
(A) 1 to 30% by weight of a higher fatty acid or a salt thereof;
(B) 0.5 to 10% by weight of a polyoxyethylene alkyl ether carboxylic acid or a salt thereof;
(C) 0.1 to 10% by weight of an amphiphilic substance having an IOB of 0.25 to 1.2;
(D) 1 to 25% by weight of a water-insoluble particle having an average particle diameter of 50 to 500 µm; and
(E) 0.05 to 1.5% by weight of a polymeric thickener,
in which:
the weight ratio between the components (A) and (B) "(A)/(B)" be 1/2 to 10/1; and
the weight ratio among the components (A), (B), and (C) "((A)+(B))/(C)" be 2/1 to 30/1.

In a further preferred embodiment, the skin cleanser according to the present invention includes:
(A) 1 to 30% by weight of a higher fatty acid or a salt thereof;
(B) 0.5 to 10% by weight of a polyoxyethylene alkyl ether carboxylic acid or a salt thereof;
(C) 0.1 to 10% by weight of an amphiphilic substance selected from the group consisting of a polyoxyethylene alkyl ether, a polyoxyethylene sorbitan fatty acid ester, a polyoxyethylene hydrogenated castor oil, and a (di)glycerin)glycerin monoalkyl ether each having an IOB of 0.25 to 1.2; and
(D) 1 to 25% by weight of a water-insoluble particle having an average particle diameter of 50 to 500 µm,
in which:
the weight ratio between the components (A) and (B) "(A)/(B)" be 1/2 to 10/1; and
the weight ratio among the components (A), (B), and (C) "((A)+(B))/(C)" be 2/1 to 30/1.

In a preferred embodiment, the skin cleanser according to the present invention includes:
(A) 1 to 30% by weight of a higher fatty acid or a salt thereof;
(B) 0.5 to 10% by weight of a polyoxyethylene alkyl ether carboxylic acid or a salt thereof;

(C) 0.1 to 10% by weight of an amphiphilic substance selected from a branched fatty acid having an IOB of 0.25 to 1.2; and (D) 1 to 25% by weight of a water-insoluble particle having an average particle diameter of 50 to 500 μm, in which:

the weight ratio between the components (A) and (B) "(A)/(B)" be 1/2 to 10/1; and the weight ratio among the components (A), (B), and (C) "((A)+(B))/(C)" be 2/1 to 30/1.

In a preferred embodiment, the skin cleanser according to the present invention includes:

(A) 1 to 30% by weight of a higher fatty acid or a salt thereof;

(B) 0.5 to 10% by weight of a polyoxyethylene alkyl ether carboxylic acid or a salt thereof;

(C) 0.1 to 10% by weight of an amphiphilic substance selected from a branched higher alcohol having an IOB of 0.25 to 1.2; and (D) 1 to 25% by weight of a water-insoluble particle having an average particle diameter of 50 to 500 μm, in which:

the weight ratio between the components (A) and (B) "(A)/(B)" be 1/2 to 10/1; and the weight ratio among the components (A), (B), and (C) "((A)+(B))/(C)" be 2/1 to 30/1.

In a further preferred embodiment, the skin cleanser according to the present invention includes:

(A) 1 to 30% by weight of a higher fatty acid or a salt thereof;

(B) 0.5 to 10% by weight of a polyoxyethylene alkyl ether carboxylic acid or a salt thereof;

(C) 0.1 to 10% by weight of an amphiphilic substance selected from a polyoxyethylene alkyl ether, a polyoxyethylene sorbitan fatty acid ester, a polyoxyethylene hydrogenated castor oil, and a (di)glycerin monoalkyl ether each having an IOB of 0.25 to 1.2; and (D) 1 to 25% by weight of a water-insoluble granulated powder having an average particle diameter of 50 to 500 μm, in which:

the weight ratio between the components (A) and (B) "(A)/(B)" be 1/2 to 10/1; and the weight ratio among the components (A), (B), and (C) "((A)+(B))/(C)" be 2/1 to 30/1.

In a further preferred embodiment, the skin cleanser according to the present invention includes:

(A) 1 to 30% by weight of a higher fatty acid or a salt thereof;

(B) 0.5 to 10% by weight of a polyoxyethylene alkyl ether carboxylic acid or a salt thereof;

(C) 0.1 to 10% by weight of an amphiphilic substance selected from the group consisting of a polyoxyethylene alkyl ether, a polyoxyethylene sorbitan fatty acid ester, a polyoxyethylene hydrogenated castor oil, and a (di)glycerin monoalkyl ether each having an IOB of 0.25 to 1.2; and (D) 1 to 25% by weight of a water-insoluble particle having an average particle diameter of 50 to 130 μm and a water-insoluble particle having an average particle diameter of 240 to 500 μm, in which:

the weight ratio "(particle having an average particle diameter of 240 to 500 μm)/(particle having an average particle diameter of 50 to 130 μm)" be 1/2 to 1/12;

the weight ratio between the components (A) and (B) "(A)/(B)" be 1/2 to 10/1; and the weight ratio among the components (A), (B), and (C) "((A)+(B))/(C)" be 2/1 to 30/1.

In the present invention, one or a combination of two or more may be used for each component.

The content of the component (A) is preferably 1 to 25% by weight, more preferably 2 to 20% by weight based on the total weight of the composition.

The content of the component (B) is preferably 1 to 8% by weight, more preferably 2 to 7% by weight based on the total weight of the composition.

The content of the component (C) is preferably 0.2 to 8% by weight, more preferably 0.3 to 5% by weight based on the total weight of the composition.

The content of the component (D) is preferably 1 to 25% by weight, more preferably 2 to 15% by weight based on the total weight of the composition.

The content of the component (E) is preferably 0.05 to 1.5% by weight, more preferably 0.2 to 1.2% by weight, even more preferably 0.4 to 0.9% by weight based on the total weight of the composition.

Further, the weight ratio between the components (A) and (B) "(A)/(B)" is 1/2 to 10/1, preferably 1/2 to 7/1.

Further, the weight ratio among the components (A), (B), and (C) "((A)+(B))/(C)" is preferably 2/1 to 30/1, more preferably 2.5/1 to 10/1.

In a preferred embodiment, the skin cleanser according to the present invention includes:

(A) 1 to 25% by weight of a higher fatty acid or a salt thereof;

(B) 1 to 8% by weight of a polyoxyethylene alkyl ether carboxylic acid or a salt thereof;

(C) 0.2 to 8% by weight of an amphiphilic substance having an IOB of 0.25 to 1.2; and (D) 2 to 15% by weight of a water-insoluble particle having an average particle diameter of 50 to 500 μm, in which:

the weight ratio between the components (A) and (B) "(A)/(B)" be 1/2 to 7/1; and the weight ratio among the components (A), (B), and (C) "((A)+(B))/(C)" be 2.5/1 to 10/1.

In a further preferred embodiment, the skin cleanser according to the present invention includes:

(A) 1 to 30% by weight of a higher fatty acid or a salt thereof;

(B) 0.5 to 10% by weight of a polyoxyethylene alkyl ether carboxylic acid or a salt thereof;

(C) 0.1 to 10% by weight of an amphiphilic substance having an IOB of 0.25 to 1.2;

(D) 1 to 25% by weight of a water-insoluble granulated powder having an average particle diameter of 50 to 130 μm and a water-insoluble granulated powder having an average particle diameter of 240 to 500 μm; and (E) 0.2 to 1.2% by weight of a polymeric thickener, in which:

the weight ratio "(granulated powder having an average particle diameter 240 to 500 μm)/(granulated powder having an average particle diameter 50 to 130 μm)" in the component (D) be 1/2 to 1/12;

the weight ratio between the components (A) and (B) "(A)/(B) " be 1/2 to 7/1; and the weight ratio among the components (A) and (B), and (C) "((A)+(B))/(C)" be 2.5/1 to 10/1.

The skin cleanser of the present invention may further contain, in addition to the above-mentioned components, components used for usual skin cleansers including a moisturizing agent such as sorbitol, an oily component, a bactericidal agent, an anti-inflammatory agent, an antiseptic, a chelating agent, a thickener, salts, a pearly sheen agent, a fragrance, a cooling agent, a dye, a UV absorber, an antioxidant, and a plant extract.

The skin cleanser of the present invention may be produced by the following method, for example. That is, first, to purified water heated to 70° C. or more are added the components (A) and (B) and the components are completely dissolved. As required, the polymeric thickener is dispersed in part of purified water and the dispersion is added to the solution. After that, the solution is neutralized with potassium hydroxide. Next, the component (C) and the component (D) are added, and the mixture is stirred to complete homogeneity, followed by cooling to room temperature, to provide the skin cleanser.

The skin cleanser of the present invention is suitable as, for example, a face wash, a body soap, or a hand soap.

EXAMPLES

Examples 1 to 28 and Comparative Examples 1 to 9

Skin cleansers having compositions shown in Table 1 to Table 4 were produced and were each evaluated for its foaming property, feeling of foam, bulkiness of foam, a feeling of particle of water-insoluble particle, cleansing effect, cleansing feeling, rinsability, and room temperature stability. Table 1 to Table 4 collectively show the results.

(Production Methods)

(1) For each of Examples 1 to 14, 18, 22, and 26, and Comparative Examples 1 and 3 to 9, to about 60% by weight of purified water heated to 70° C. or more were added the components (A) and (B), and the components were completely dissolved. Next, potassium hydroxide was added in an amount enough to neutralize the components (A) and (B), and the mixture was stirred to homogeneity. The component (C) was further added and the whole was stirred to give a homogenous solution. After that, the solution was cooled to room temperature. To the solution was added a liquid prepared by dispersing the component (D) in a mixed liquid of balance water and sorbitol, and the mixture was stirred until the component (D) was uniformly dispersed to provide a target skin cleanser.

(2) For each of Examples 15, 20, 23, 24, 27, and 28, and Comparative Example 2, to about 40% by weight of purified water heated to 70° C. or more were added the components (A) and (B), and the components were completely dissolved. Next, the component (E) was dispersed in 20% by weight of water, and the dispersion was added to the solution. Potassium hydroxide was added in an amount enough to neutralize the components (A), (B), and (E), and the mixture was stirred to homogeneity. The component (C) was further added and the whole was stirred to give a homogeneous solution. After that, the solution was cooled to room temperature. To the solution was added a liquid prepared by dispersing the component (D) in a mixed liquid of balance water and sorbitol, and the mixture was stirred until the component (D) was uniformly dispersed to provide a target skin cleanser.

(3) For each of Examples 16, 17, 19, 21, and 25, to about 25% by weight of purified water heated to 70° C. or more were added the components (A) and (B), and the components were completely dissolved. Next, the component (E) was dispersed in 20% by weight of water, and the dispersion was added to the solution. After lauryl hydroxysultaine had been further added, potassium hydroxide was added in an amount enough to neutralize the components (A), (B), and (E), and the mixture was stirred to homogeneity. The component (C) other than glycerin mono-2-ethylhexyl ether was further added and the whole was stirred to give a homogeneous solution. After that, the solution was cooled to room temperature. To the solution was added a liquid prepared by dispersing the component (D) in a mixed liquid of balance water and sorbitol, and the mixture was stirred until the component (D) was uniformly dispersed. After that, glycerin mono-2-ethylhexyl ether as the component (C) was added, and the mixture was stirred until the component was uniformly dispersed to provide a target skin cleanser.

(Evaluation Methods)

(1) Foaming Property

Each skin cleanser was actually used by five trained panelists, and foamed with hands. A sensory evaluation was made of foaming property in this case based on five-grade evaluation criteria shown in (I), and the average of scores marked by the respective panelists was determined.

(I) Five-Grade Evaluation Criteria;
  5; Good foaming property.
  4; Slightly good foaming property.
  3; Neutral.
  2; Slightly poor foaming property
  1; Poor property (2) Feeling of Foam Each skin cleanser was actually used by five trained panelists, and foamed with hands. The foam was used to massage the face. A sensory evaluation was made of softness of the foam in this case based on five-grade evaluation criteria shown in (II), and the average of scores marked by the respective panelists was determined.

(II) Five-Grade Evaluation Criteria;
  5; The foam is good in softness.
  4; The foam is slightly good in softness.
  3; Neutral.
  2; The foam is slightly poor in softness.
  1; The foam is poor in softness.

(3) Bulkiness of Foam (Foam Density)

Each skin cleanser was actually used by five trained panelists, and rubbed against the palm for 30 reciprocations to produce foam. A sensory evaluation was made of bulkiness of the foam based on five-grade evaluation criteria shown in (III), and the average of scores marked by the respective panelists was determined.

(III) Five-Grade Evaluation Criteria;
  5; Foam containing a large amount of air (bubbly).
  4; Foam containing a slightly large amount of air.
  3; Foam containing air.
  2; Foam containing little air.
  1; Foam containing no air (creamy).

(4) Feeling of Particle of Water-Insoluble Particles 1 g of each skin cleanser was picked up by each of five trained panelists, foamed by the addition of a small amount of water and rubbing with hands ten times. After that, the palm of one hand was pressed against the back of the other hand. A sensory evaluation was made of feeling of particle of water-insoluble particles in this case based on five-grade evaluation criteria shown in (IV), and the average of scores marked by the respective panelists was determined.

Also in the case of foaming the cleanser in the same manner as above except for rubbing 30 times, a sensory evaluation was made based on the five-grade evaluation criteria shown in (IV), and the average of scores marked by the respective panelists was determined.

(IV) Five-Grade Evaluation Criteria;
  5; Clear feeling of particle.
  4; Feeling of particle.
  3; Slight feeling of particle.
  2; Not much feeling of particle.
  1; No feeling of particle.

(5) Cleansing Effect

A circle having an area of 7 $cm^2$ is drawn on the medial side of a human forearm, and the area is subjected to colorimetry (reference color) with a chromatic-difference meter (CR-200, manufactured by Minolta). 20 µL of model keratotic plug (Table 5) colored black with carbon black are applied to the area, and left to stand for 30 minutes. After that, excess model keratotic plug on the surface is removed with a spatula made of stainless steel. At this time, a color difference (ΔE1) is measured and its value is confirmed to fall within the range of 20 to 25. (If the value exceeds the range, excess model keratotic plug is removed again with the spatula until the ΔE1 value becomes 20 to 25.) 1 g of each skin cleanser was rubbed against the palm for 30 reciprocations to foam the cleanser. 0.5 g of the foam was used to perform cleansing by massaging the area 30 times, and was then rinsed with tap water. After the cleansing, colorimetry was performed again for a color difference with respect to the reference color (ΔE2), and cleansing power was determined from the following equation. The procedure was repeated five times for each skin cleanser, and the average thereof was determined.

$$\text{Cleansing power (\%)} = \frac{(\Delta E1 - \Delta E2)}{\Delta E1} \times 100$$

(6) Cleansing Feeling 1 g of each skin cleanser was applied by each of five trained panelists on each of their hands, foamed by the addition of a small amount of water to wash the face, and then rinsed with tap water. After towel drying, a sensory evaluation was made of cleansing feeling based on five-grade evaluation criteria shown in (V), and the average of scores marked by the respective panelists was determined.

(V) Five-Grade Evaluation Criteria;
5; Very intense feeling of dirt removal.
4; Feeling of dirt removal.
3; Slight feeling of dirt removal.
2; Not much feeling of dirt removal.
1; No feeling of dirt removal.

(7) Rinsability 1 g of each skin cleanser was picked up by each of five trained panelists, foamed by the addition of a small amount of water to wash the face, and then rinsed with tap water. A sensory evaluation was made of rinsability in this case based on five-grade evaluation criteria shown in (VI), and the average of scores marked by the respective panelists was determined.

(VI) Five-Grade Evaluation Criteria;
5; Good rinsability.
4; Slightly good rinsability.
3; Neutral.
2; Slightly poor rinsability.
1; Poor rinsability.

(8) Room Temperature Stability 100 g of each skin cleanser were loaded into a glass bottle having a volume of 130 mL, and left to stand for 1 day at room temperature. After that, a suspension (or precipitation) state of the water-insoluble particles in the skin cleanser was visually observed based on three-grade evaluation criteria shown in (VII) to determine scores.

(VII) Three-Grade Evaluation Criteria;
A; The water-insoluble particles are uniformly dispersed.
B; The water-insoluble particles are in a nonuniform state, but can be easily redispersed uniformly.
C; The water-insoluble particles are in a nonuniform state, and cannot be redispersed.

TABLE 1

| Component (% by weight) | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|---|---|---|---|---|
| (A) Lauric acid[1] | 7 | 1.1 | 0.9 | 8.7 | 7 | 7 | 7 | 7 | 7 | 7 | 7 | 7 | 7 | 7 |
| (A) Myristic acid[2] | 2.4 | 3.3 | 2.6 | 3 | 2.4 | 2.4 | 2.4 | 2.4 | 2.4 | 2.4 | 2.4 | 2.4 | 2.4 | 2.4 |
| (A) Palmitic acid[3] | 0.6 | 2.5 | | 0.7 | 0.6 | 0.6 | 0.6 | 0.6 | 0.6 | 0.6 | 0.6 | 0.6 | 0.6 | 0.6 |
| (A) Stearic acid[4] | | 3.1 | 4.5 | | | | | | | | | | | |
| (A) Behenic acid[5] | | | 2 | | | | | | | | | | | |
| (B) Laureth-6 carboxylic acid[6] | 4 | 4 | 4 | 1.6 | 4 | 4 | 4 | 4 | 4 | 4 | 4 | 4 | 4 | 4 |
| (B) Sodium laureth-4 carboxylate[7] | | | | | | | | | | | | | | |
| (B) Sodium laureth-11 carboxylate[8] | | | | | | | | | | | | | | |
| Potassium hydroxide | 3.1 | 2.7 | 2.5 | 3.5 | 3.1 | 3.1 | 3.1 | 3.1 | 3.1 | 3.1 | 3.1 | 3.1 | 3.1 | 3.1 |
| (C) Polyoxyethylene monoalkyl ether (3.3E.O.)[9] (IOB = 0.89, Mw = 345) | 3 | 3 | 3 | 3 | 1 | | | | | | | | 3 | 3 |
| (C) Polyoxyethylene sorbitan monostearate (6E.O.)[10] (IOB = 1.15, Mw = 694) | | | | | | 3 | | | | | | | | |
| (C) Polyoxyethylene octyl dodecyl ether (5E.O.)[11] (IOB = 0.81, Mw = 518) | | | | | | | 3 | | | | | | | |
| (C) Polyoxyethylene octyl dodecyl ether (10E.O.)[12] (IOB = 1.08, Mw = 738) | | | | | | | | 3 | | | | | | |
| (C) Polyoxyethylene hydrogenated castor oil (7E.O.)[13] (IOB = 0.71, Mw = 1,245) | | | | | | | | | 3 | | | | | |
| (C) Polyoxyethylene isostearyl ether (5E.O.)[14] (IOB = 0.86, Mw = 490) | | | | | | | | | | 3 | | | | |
| (C) Polyoxyethylene isostearyl ether (10E.O.)[15] (IOB = 1.13, Mw = 710) | | | | | | | | | | | 3 | | | |
| (C) Isostearic acid[16] (IOB = 0.43, Mw = 284) | | | | | | | | | | | | 3 | | |
| (C) 2-Octyldodecanol[17] (IOB = 0.26, Mw = 298) | | | | | | | | | | | | | | |
| (C) Glycerin monocaprate[18] (IOB = 1.18, Mw = 246) | | | | | | | | | | | | | | |
| (C) Glycerin mono-2-ethylhexyl ether[19] (IOB = 1.05, Mw = 204) | | | | | | | | | | | | | | |
| (D) Disintegrable particle (average particle diameter: 300 μm)[20] | 5 | 5 | 5 | 5 | 5 | 5 | 5 | 5 | 5 | 5 | 5 | 5 | | 2.5 |
| (D) Disintegrable particle (average particle diameter: 100 μm)[20] | | | | | | | | | | | | | 10 | 7.5 |
| (D) Disintegrable particle (average particle diameter: 500 μm)[20] | | | | | | | | | | | | | | |
| (D) TexPURE 400E (average particle diameter: 55 μm)[21] | | | | | | | | | | | | | | |

TABLE 1-continued

| Component (% by weight) | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 |
|---|---|---|---|---|---|---|---|---|---|---|---|---|---|---|
| (D) TexPURE 500E (average particle diameter: 75 μm)[21] | | | | | | | | | | | | | | |
| (D) TexPURE 700E (average particle diameter: 130 μm)[21] | | | | | | | | | | | | | | |
| (D) TexPURE 1200P (average particle diameter: 240 μm)[22] | | | | | | | | | | | | | | |
| (D) Inducos 14/2 (average particle diameter: 400 μm)[23] | | | | | | | | | | | | | | |
| (D) Ceolus PH101 (average particle diameter: 50 μm)[24] | | | | | | | | | | | | | | |
| (D) Asensa™ SC231 (average particle diameter: 125 μm)[25] | | | | | | | | | | | | | | |
| (D) Asensa™ SC400 (average particle diameter: 350 μm)[26] | | | | | | | | | | | | | | |
| (E) Acrylic acid/alkyl methacrylate copolymer[27] | | | | | | | | | | | | | | |
| Lauryl hydroxysultaine[28] | | | | | | | | | | | | | | |
| Sorbitol[29] | 14 | 14 | 14 | 14 | 14 | 14 | 14 | 14 | 14 | 14 | 14 | 14 | 14 | 14 |
| Water | Balance | Balance | Balance | Balance | Balance | Balance | Balance | Balance | Balance | Balance | Balance | Balance | Balance | Balance |
| Total | 100 | 100 | 100 | 100 | 100 | 100 | 100 | 100 | 100 | 100 | 100 | 100 | 100 | 100 |
| (A)/(B) | 2.5/1 | 2.5/1 | 2.5/1 | 7.8/1 | 2.5/1 | 2.5/1 | 2.5/1 | 2.5/1 | 2.5/1 | 2.5/1 | 2.5/1 | 2.5/1 | 2.5/1 | 2.5/1 |
| ((A) + (B))/(C) | 4.7/1 | 4.7/1 | 4.7/1 | 4.7/1 | 14/1 | 4.7/1 | 4.7/1 | 4.7/1 | 4.7/1 | 4.7/1 | 4.7/1 | 4.7/1 | 4.7/1 | 4.7/1 |
| Foaming property | 4.0 | 4.2 | 4.0 | 4.2 | 4.6 | 4.0 | 4.0 | 4.0 | 4.0 | 4.0 | 4.0 | 3.8 | 4.0 | 4.0 |
| Feeling of foam (softness) | 4.6 | 4.2 | 4.4 | 4.2 | 4.4 | 4.0 | 4.6 | 4.4 | 4.4 | 4.6 | 4.6 | 4.6 | 4.6 | 4.6 |
| Bulkiness of foam (foam density) | 4.8 | 4.6 | 4.6 | 4.4 | 4.4 | 4.2 | 4.8 | 4.2 | 4.2 | 4.8 | 4.2 | 4.8 | 4.8 | 4.8 |
| Feeling of particle of scrub (rubbed with palms 10 times) | 4.8 | 4.8 | 4.8 | 4.6 | 4.6 | 4.8 | 4.8 | 4.8 | 4.8 | 4.8 | 4.8 | 4.8 | 4.8 | 4.8 |
| Feeling of particle of scrub (rubbed with palms 30 times) | 4.6 | 4.2 | 4.2 | 4.0 | 4.0 | 4.0 | 4.6 | 4.0 | 4.0 | 4.6 | 4.0 | 4.6 | 4.6 | 4.6 |
| Cleansing effect (%) | 85 | 83 | 83 | 82 | 81 | 84 | 83 | 83 | 84 | 84 | 83 | 83 | 86 | 92 |
| Cleansing feeling | 4.6 | 4.4 | 4.6 | 4.6 | 4.6 | 4.2 | 4.0 | 4.0 | 4.2 | 4.2 | 4.0 | 4.6 | 4.6 | 4.8 |
| Rinsability | 4.0 | 4.2 | 4.2 | 4.4 | 4.6 | 4.0 | 4.0 | 4.0 | 4.0 | 4.0 | 4.0 | 4.0 | 4.0 | 4.0 |
| Room temperature stability (precipitation or suspension of scrub particles) | B | B | B | B | B | B | B | B | B | B | B | B | B | B |

TABLE 2

[1] Lunac L-98 (manufactured by Kao Corporation)
[2] Lunac MY-98 (manufactured by Kao Corporation)
[3] Lunac P-95 (manufactured by Kao Corporation)
[4] Lunac S-98 (manufactured by Kao Corporation)
[5] Lunac BA (manufactured by Kao Corporation)
[6] Active ingredient of Kao Akypo RML-45 (polyoxyethylene lauryl ether acetate) (90%) (manufactured by Kao Corporation)
[7] Active ingredient of Beaulight LCA (sodium polyoxyethylene lauryl ether acetate) (92%) (manufactured by Sanyo Chemical Industries, Ltd.)
[8] Active ingredient of Kao Akypo RML-45NV (sodium polyoxyethylene lauryl ether acetate) (24%) (manufactured by Kao Corporation)
[9] Softanol 33 (manufactured by NIPPON SHOKUBAI CO., LTD.)
[10] Rheodol TW-S 106V (manufactured by Kao Corporation)
[11] EMALEX OD-5 (manufactured by NIHON EMULSION Co., Ltd.)
[12] EMALEX OD-10 (manufactured by NIHON EMULSION Co., Ltd.)
[13] EMALEX HC-7 (manufactured by NIHON EMULSION Co., Ltd.)
[14] EMALEX 1805 (manufactured by NIHON EMULSION Co., Ltd.)
[15] EMALEX 1810 (manufactured by NIHON EMULSION Co., Ltd.)
[16] Isostearic acid (manufactured by NISSAN CHEMICAL INDUSTRIES, LTD.)
[17] Kalcol 200GD (manufactured by Kao Corporation)
[18] Homotex PT (manufactured by Kao Corporation)

TABLE 2-continued

[19] Active ingredient of Penetol GE-EH (90%) (manufactured by Kao Corporation)
[20] Disintegrable particles obtained by the method described in Production Example 3 of JP-A-2000-119171 (cellulose powder:corn starch:maleic acid-modified polyvinyl alcohol = 50:50:10), specific gravity: 1.7
[21] TexPure 400E, 500E, 700E (manufactured by SHAMROCK TECHNOLOGIES, Inc.) (polyethylene)
[22] TexPure 1200P (manufactured by SHAMROCK TECHNOLOGIES, Inc.) (polypropylene)
[23] Inducos 14/2 (manufactured by Induchem) (polyethylene)
[24] Ceolus PH101 (manufactured by Asahi Kasei Chemicals Corporation) (crystalline cellulose)
[25] Asensa™ SC231 (manufactured by Honeywell) (polyethylene oxide)
[26] Asensa™ SC400 (manufactured by Honeywell) (ethylene-acrylic acid copolymer (EAA))
[27] Carbopol ETD 2020 (manufactured by NOVEON)
[28] Active ingredient of AMPHITOL 20HD (30%) (manufactured by Kao Corporation)
[29] Active ingredient of Sorbitol Kao (70%) (manufactured by Kao Corporation)
[30] Softanol 90 (manufactured by NIPPON SHOKUBAI CO., LTD.)
[31] EMALWX OD-20 (manufactured by NIHON EMULSION Co., Ltd.)

TABLE 3

| Component (% by weight) | Ex. 15 | Ex. 16 | Ex. 17 | Ex. 18 | Ex. 19 | Ex. 20 | Ex. 21 | Ex. 22 | Ex. 23 | Ex. 24 | Ex. 25 | Ex. 26 | Ex. 27 | Ex. 28 |
|---|---|---|---|---|---|---|---|---|---|---|---|---|---|---|
| (A) Lauric acid[1] | 7 | 7 | 1 | 21 | 2.1 | 7 | 1 | 17.5 | 2.1 | 4.9 | 1.4 | 14 | 2.1 | 5.6 |
| (A) Myristic acid[2] | 2.4 | 2.4 | | 7.2 | 0.7 | 2.4 | | 6 | 0.7 | 1.7 | 0.5 | 4.8 | 0.7 | 1.9 |
| (A) Palmitic acid[3] | 0.6 | 0.6 | | 1.8 | 0.2 | 0.6 | | 1.5 | 0.2 | 0.4 | 0.1 | 1.2 | 0.2 | 0.5 |
| (A) Stearic acid[4] | | | | | | | | | | | | | | |
| (A) Behenic acid[5] | | | | | | | | | | | | | | |

TABLE 3-continued

| Component (% by weight) | Ex. 15 | Ex. 16 | Ex. 17 | Ex. 18 | Ex. 19 | Ex. 20 | Ex. 21 | Ex. 22 | Ex. 23 | Ex. 24 | Ex. 25 | Ex. 26 | Ex. 27 | Ex. 28 |
|---|---|---|---|---|---|---|---|---|---|---|---|---|---|---|
| (B) Laureth-6 carboxylic acid*[6] | 4 | 4 | 0.5 | | 6 | 1 | 1 | | 6 | 1 | 2 | | 4 | 2 |
| (B) Sodium laureth-4 carboxylate*[7] | | | | | | | | | | | | | | |
| (B) Sodium laureth-11 carboxylate*[8] | | | | 10 | | | | 8 | | | | 7 | | |
| Potassium hydroxide | 3.5 | 3.5 | 0.5 | 7.4 | 2.4 | 2.6 | 0.6 | 6.1 | 2.2 | 2.0 | 0.9 | 4.9 | 1.8 | 2.5 |
| (C) Polyoxyethylene monoalkyl ether (3.3E.O.)*[9] (IOB = 0.89, Mw = 345) | 3 | 3 | | 10 | | | | 8 | | | | 5 | 1 | 3.3 |
| (C) Polyoxyethylene sorbitan monostearate (6E.O.)*[10] (IOB = 1.15, Mw = 694) | | | | | | | | | | | | | | |
| (C) Polyoxyethylene octyl dodecyl ether (5E.O.)*[11] (IOB = 0.81, Mw = 518) | | | | | | | | | | | | | | |
| (C) Polyoxyethylene octyl dodecyl ether (10E.O.)*[12] (IOB = 1.08, Mw = 738) | | | | | | | | | | | | | | |
| (C) Polyoxyethylene hydrogenated castor oil (7E.O.)*[13] (IOB = 0.71, Mw = 1,245) | | | | | | | | | | | | | | |
| (C) Polyoxyethylene isostearyl ether (5E.O.)*[14] (IOB = 0.86, Mw = 490) | | | | | | | | | | | | | | |
| (C) Polyoxyethylene isostearyl ether (10E.O.)*[15] (IOB = 1.13, Mw = 710) | | | | | | | | | | | | | | |
| (C) Isostearic acid*[16] (IOB = 0.43, Mw = 284) | | | | | | | | | | | | | | |
| (C) 2-Octyldodecanol*[17] (IOB = 0.26, Mw = 298) | | | | | | | | | | | | | | |
| (C) Glycerin monocaprate*[18] (IOB = 1.18, Mw = 246) | | | | | | 5.5 | | | 0.9 | 3.2 | | | | |
| (C) Glycerin mono-2-ethylhexyl ether*[19] (IOB = 1.05, Mw = 204) | | 1 | 0.1 | | 0.1 | | 0.2 | | | | 0.3 | | | |
| (D) Disintegrable particle (average particle diameter: 300 μm)*[20] | 5 | 2.5 | | 3 | | | | 3 | | 3 | | 2.5 | 2.5 | 2.5 |
| (D) Disintegrable particle (average particle diameter: 100 μm)*[20] | | 7.5 | | | | | | | | | | 7.5 | 5 | 10 |
| (D) Disintegrable particle (average particle diameter: 500 μm)*[20] | | | | 1.92 | | | | | | | | | | |
| (D) TexPURE 400E (average particle diameter: 55 μm)*[21] | | | | | | | | | | | | | | |
| (D) TexPURE 500E (average particle diameter: 75 μm)*[21] | | | | | | | | 13.64 | | | | | | |
| (D) TexPURE 700E (average particle diameter: 130 μm)*[21] | | | | | | 3.33 | | | | | | | | |
| (D) TexPURE 1200P (average particle diameter: 240 μm)*[22] | | | | | | 1.67 | | | | 1.25 | | | | |
| (D) Inducos 14/2 (average particle diameter: 400 μm)*[23] | | | 1 | | | | 2 | | | | | | | |
| (D) Ceolus PH101 (average particle diameter: 50 μm)*[24] | | | | 23.08 | | | | | | | | | | |
| (D) Asensa ™ SC231 (average particle diameter: 125 μm)*[25] | | | | | | | | | | | 3.75 | | | |
| (D) Asensa ™ SC400 (average particle diameter: 350 μm)*[26] | | | | | | | | 1.36 | | | | | | |
| (E) Acrylic acid/alkyl methacrylate copolymer*[27] | 0.6 | 0.6 | 0.3 | | 1.5 | 0.05 | 0.3 | | 1.2 | 0.2 | 0.3 | | 0.9 | 0.4 |
| Lauryl hydroxysultaine*[28] | | 4.5 | 3 | | 3 | 3 | 3 | | 3 | 3 | 3 | | 3 | 3 |
| Sorbitol*[29] | 14 | 14 | 14 | | 14 | 14 | 14 | | 14 | 14 | 14 | 14 | 14 | 14 |
| Water | Balance | Balance | Balance | Balance | Balance | Balance | Balance | Balance | Balance | Balance | Balance | Balance | Balance | Balance |
| Total | 100 | 100 | 100 | 100 | 100 | 100 | 100 | 100 | 100 | 100 | 100 | 100 | 100 | 100 |
| (A)/(B) | 2.5/1 | 2.5/1 | 2/1 | 3/1 | 1/2 | 10/1 | 1/1 | 3.3/1 | 1/2 | 7/1 | 1/1 | 2.9/1 | 1/1.5 | 4/1 |
| ((A) + (B))/(C) | 4.7/1 | 3.5/1 | 15/1 | 4/1 | 30/1 | 2/1 | 10/1 | 4.3/1 | 10/1 | 2.5/1 | 13.3/1 | 5.4/1 | 7/1 | 3/1 |
| Foaming property | 4.0 | 4.2 | 4.0 | 3.9 | 3.8 | 4.6 | 4.0 | 4.0 | 4.0 | 4.1 | 4.0 | 4.0 | 4.0 | 4.3 |
| Feeling of foam (softness) | 4.6 | 4.4 | 3.8 | 3.8 | 4.6 | 4.4 | 3.8 | 3.8 | 4.6 | 4.1 | 3.9 | 3.9 | 4.6 | 4.3 |
| Bulkiness of foam (foam density) | 4.8 | 5.0 | 3.7 | 3.7 | 3.6 | 4.4 | 3.8 | 3.8 | 3.7 | 4.1 | 3.9 | 3.9 | 3.8 | 4.3 |
| Feeling of particle of scrub (rubbed with palms 10 times) | 4.8 | 4.8 | 4.8 | 4.8 | 4.6 | 4.8 | 4.8 | 4.8 | 4.8 | 4.8 | 4.8 | 4.8 | 4.8 | 4.8 |
| Feeling of particle of scrub (rubbed with palms 30 times) | 4.6 | 4.4 | 4.0 | 4.0 | 4.1 | 4.2 | 4.2 | 4.1 | 4.2 | 4.4 | 4.4 | 4.2 | 4.4 | 4.6 |
| Cleansing effect (%) | 86 | 90 | 75 | 80 | 78 | 81 | 76 | 81 | 78 | 84 | 79 | 82 | 83 | 85 |
| Cleansing feeling | 4.6 | 5.0 | 3.8 | 4.0 | 3.9 | 4.2 | 3.9 | 4.2 | 4.2 | 4.4 | 4.2 | 4.2 | 4.4 | 4.6 |
| Rinsability | 4.0 | 4.0 | 4.2 | 4.4 | 4.0 | 4.0 | 4.2 | 4.4 | 4.0 | 4.0 | 4.2 | 4.4 | 4.0 | 4.0 |
| Room temperature stability (precipitation or suspension of scrub particles) | A | A | B | A | A | B | B | A | A | B | A | A | B | B |

TABLE 4

| Component (% by weight) | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| (A) Lauric acid*[1] | 9.8 | 9.8 | 7 | 2.5 | 9.1 | 2.5 | 2.5 | 7 | 7 |
| (A) Myristic acid*[2] | 3.4 | 3.4 | 2.4 | 0.8 | 3.1 | 0.8 | 0.8 | 2.4 | 2.4 |
| (A) Palmitic acid*[3] | 0.8 | 0.8 | 0.6 | 0.2 | 0.8 | 0.2 | 0.2 | 0.6 | 0.6 |
| (B) Laureth-6 carboxylic acid*[6] | | | 4 | 10.5 | 1 | 10.5 | 10.5 | 4 | 4 |
| Potassium hydroxide | 4.2 | 4.1 | 3.1 | 2 | 3.6 | 2 | 2 | 3.1 | 3.1 |
| (C) Polyoxyethylene monoalkyl ether (3.3E.O.)*[9] (IOB = 0.89, Mw = 345) | | | | | | 3 | 0.39 | | |
| (C) Polyoxyethylene monoalkyl ether (9E.O.)*[30] (IOB = 1.25, Mw = 596) | | | | | | | | 3 | |
| (C) Polyoxyethylene octyl dodecyl ether (20E.O.)*[31] (IOB = 1.34, Mw = 1,178) | | | | | | | | | 3 |
| (D) Disintegrable particle (average particle diameter: 300 μm)*[20] | 5 | 5 | 5 | 5 | 5 | 5 | 5 | 5 | 5 |
| (E) Acrylic acid/alkyl methacrylate copolymer*[28] | | 0.6 | | | | | | | |
| Sorbitol*[29] | 14 | 14 | 14 | 14 | 14 | 14 | 14 | 14 | 14 |
| Water | Balance | Balance | Balance | Balance | Balance | Balance | Balance | Balance | Balance |
| Total | 100 | 100 | 100 | 100 | 100 | 100 | 100 | 100 | 100 |
| (A)/(B) | — | — | 2.5/1 | 1/3 | 13/1 | 1/3 | 1/3 | 2.5/1 | 2.5/1 |
| ((A) + (B))/(C) | — | — | — | — | — | 4.7/1 | 35/1 | 4.7/1 | 4.7/1 |
| Foaming property | 5.0 | 5.0 | 4.8 | 4.6 | 5.0 | 1.4 | 4.2 | 4.4 | 4.4 |
| Feeling of foam (softness) | 3.0 | 3.0 | 3.6 | 4.8 | 3.4 | 2.4 | 4.8 | 4.0 | 4.0 |
| Bulkiness of foam (foam density) | 2.0 | 1.8 | 3.0 | 3.2 | 2.8 | 2.6 | 4.0 | 3.8 | 3.6 |
| Feeling of particle of scrub (rubbed with palms 10 times) | 3.0 | 3.0 | 3.6 | 4.0 | 3.2 | 5.0 | 4.6 | 4.4 | 4.4 |
| Feeling of particle of scrub (rubbed with palms 30 times) | 1.0 | 1.4 | 2.0 | 2.2 | 1.6 | 5.0 | 2.8 | 2.6 | 2.6 |
| Cleansing effect (%) | 69 | 70 | 71 | 72 | 70 | 88 | 74 | 72 | 73 |
| Cleansing feeling | 3.2 | 3.4 | 3.0 | 3.0 | 3.6 | 2.8 | 3.0 | 3.8 | 3.8 |
| Rinsability | 5.0 | 5.0 | 4.8 | 3.0 | 5.0 | 2.4 | 2.8 | 4.0 | 4.0 |
| Room temperature stability (precipitation or suspension of scrub particles) | B | A | B | B | B | B | B | B | B |

TABLE 5

(Model keratotic plug)

| (Component) | (% by weight) |
|---|---|
| Squalene | 7.84 |
| Myristyl myristate | 13.73 |
| Cotton seed oil | 7.06 |
| Cholesterol | 11.76 |
| Cholesterol palmitate | 3.92 |
| Lauric acid | 0.78 |
| Myristic acid | 6.27 |
| Palmitic acid | 23.54 |
| Stearic acid | 4.71 |
| Oleic acid | 18.43 |
| Carbon black | 1.96 |

Example 29

Skin Cleanser (Face Wash)

A skin cleanser having the following composition was produced by the same method as the production method (3) for Examples 1 to 28 based on the following blend composition.

The resultant skin cleanser was subjected to the evaluations and showed excellent results in all of the evaluations.

| (Components) | |
|---|---|
| (1) Lauric acid*[1] | 7.0 (% by weight) |
| (2) Myristic acid*[2] | 2.4 |
| (3) Palmitic acid*[3] | 0.6 |
| (4) Sodium laureth-4 carboxylate*[7] | 4.0 |
| (5) Potassium hydroxide | 2.9 |
| (6) Glycerin mono-2-ethylhexyl ether*[19] (IOB = 1.05, Mw = 204) | 2.5 |
| (7) 2-Octyldodecanol*[17] (IOB = 0.26, Mw = 298) | 1.0 |
| (8) Inducos 14/2 (average particle diameter: 400 μm)*[23] | 2.0 |
| (9) TexPure 400E (average particle diameter: 55 μm)*[21] | 10.0 |
| (10) Acrylic acid/alkyl methacrylate copolymer*[27] | 0.6 |
| (11) Lauryl hydroxysultaine*[28] | 3.0 |
| (12) Sorbitol*[29] | 14.0 |
| (13) Purified water | Balance |
| Total | 100.0 |

Example 30

Skin Cleanser (Body Soap)

A skin cleanser having the following composition was produced by the same method as the production method (2) for Examples 1 to 28 based on the following blend composition.

The resultant skin cleanser was subjected to the evaluations and showed excellent results in all of the evaluations.

| (Components) | |
|---|---|
| (1) Lauric acid*[1] | 4.0 (% by weight) |
| (2) Myristic acid*[2] | 1.5 |
| (3) Palmitic acid*[3] | 0.3 |
| (4) Laureth-6 carboxylic acid*[6] | 1.8 |
| (5) Potassium hydroxide | 2.2 |
| (6) Glycerin monocaprate*[18] (IOB = 1.18, Mw = 246) | 1.0 |
| (7) Disintegrable particle (average particle diameter: 500 μm)*[20] | 5.0 |
| (8) Acrylic acid/alkyl methacrylate copolymer*[27] | 0.6 |
| (9) Lauryl hydroxysultaine*[28] | 1.5 |
| (10) Sorbitol*[29] | 12.0 |
| (11) Purified water | Balance |
| Total | 100.0 |

The invention claimed is:

1. A skin cleanser, comprising the following components (A) to (D):
   (A) from 1 to 30% by weight of a fatty acid or a salt thereof comprising a linear alkyl group having from 11 to 23 carbon atoms;
   (B) from 0.5 to 10% by weight of a polyoxyethylene alkyl ether carboxylic acid or a salt thereof;
   (C) from 0.1 to 10% by weight of an amphiphilic substance, wherein the amphiphilic substance is at least one selected from the group consisting of a polyoxyethylene alkyl ether, polyoxyethylene sorbitan fatty acid ester, a polyoxyethylene hydrogenated castor oil, a (di)glycerin monofatty acid ester, a (di)glycerin monoalkyl ether, a branched fatty acid, and a branched higher alcohol, wherein the amphiphilic substance has an iorganic organic balance value (IOB) of from 0.25 to 1.2; and
   (D) from 1 to 25% by weight of water-insoluble particles having an average particle diameter of from 50 to 500 μm, wherein the water-insoluble particles are a water-insoluble powder selected from the group consisting of an inorganic powder, a silicone powder, a silk powder, a hemp powder, an organic powder of saccharide, a synthetic polymer, and a granulated powder obtained by using the water-insoluble particles as primary particles and a binder,
   wherein a weight ratio between the components (A) and (B), (A)/(B), is from 1/2 to 10/1.

2. The skin cleanser according to claim 1, wherein a weight ratio among the components (A), (B), and (C), ((A)+(B))/(C), is from 2/1 to 30/1.

3. The skin cleanser according to claim 1, wherein the component (C) comprises an amphiphilic substance having a molecular weight of 500 or less.

4. The skin cleanser according to claim 3, wherein the component (C) comprises at least one amphiphilic substance selected from the group consisting of a polyoxyethylene alkyl ether, a polyoxyethylene sorbitan fatty acid ester, a polyoxyethylene hydrogenated castor oil, and a (di)glycerin monoalkyl ether.

5. The skin cleanser according to claim 3, wherein the component (C) comprises an amphiphilic substance selected from a branched fatty acid.

6. The skin cleanser according to claim 3, wherein the component (C) comprises an amphiphilic substance selected from a branched higher alcohol.

7. The skin cleanser according to claim 1, wherein the water-insoluble particles comprise a water-insoluble particle having an average particle diameter of from 50 to 130 μm and a water-insoluble particle having an average particle diameter of from 240 to 500 μm.

8. The skin cleanser according to claim 1, wherein the water-insoluble particles comprise a water-insoluble granulated powder.

9. The skin cleanser according claim 1, further comprising (E) from 0.05 to 1.5% by weight of a polymeric thickener.

10. The skin cleanser according claim 1, comprising at least one inorganic powder as the water-insoluble particles selected form the group consisting of titanium dioxide, talc, kaolin, bentonite, sodium chloride, silica, and mica titanium.

11. The skin cleanser according claim 1, comprising at least one organic powder as the water-insoluble particles selected form the group consisting of cellulose and a derivative thereof.

12. The skin cleanser according claim 1, comprising at least one synthetic polymer as the water-insoluble particles selected form the group consisting of polyethylene, polypropylene, polyethylene oxide, an ethylene-acrylic acid copolymer, polystyrene, nylon, and an acrylic resin.

13. The skin cleanser according claim 1, comprising the granulated powder as the water-insoluble particles obtained by using the water-insoluble particles as primary particles and the binder selected form the group consisting of a synthetic product, a semisynthetic product, and a natural polymer.

14. The skin cleanser according to claim 13, wherein the binder is at least one synthetic product selected form the group consisting of a polyvinyl alcohol and a derivative thereof; a poly(meth)acrylic acid alkali salt; an alkali salt of a (meth)acrylic acid ester copolymer; an alkali salt of an acrylic acid/maleic acid copolymer, and polyvinylpyrrolidone.

15. The skin cleanser according claim 13, wherein the binder is at least one semisynthetic product selected form the group consisting of methylcellulose, ethylcellulose, carboxymethylcellulose, hydroxyalkylcellulose, and a starch derivative.

16. The skin cleanser according to claim 13, wherein the binder is at least one natural polymer selected form the group consisting of starch, seaweed, plant mucus, and a protein.

17. The skin cleanser according to claim 1, comprising the water-insoluble particles selected from the group consisting of polyethylene, polypropylene, crystalline cellulose, and ethylene-acrylic acid copolymer particles.

18. The skin cleanser according to claim 1, comprising the water-insoluble particles selected from the group consisting of polypropylene, and ethylene-acrylic acid copolymer particles.

19. The skin cleanser according claim 1, wherein the water-insoluble particles are ethylene-acrylic acid copolymer (EAA).

* * * * *

UNITED STATES PATENT AND TRADEMARK OFFICE
CERTIFICATE OF CORRECTION

PATENT NO.         : 8,815,787 B2                        Page 1 of 1
APPLICATION NO.    : 13/512049
DATED              : August 26, 2014
INVENTOR(S)        : Shinichi Ikegaki et al.

It is certified that error appears in the above-identified patent and that said Letters Patent is hereby corrected as shown below:

In the Claims

Column 20, line 12, "according claim 1," should read --according to claim 1,--;
line 14, "according claim 1," should read --according to claim 1,--;
line 19, "according claim 1," should read --according to claim 1,--;
line 23, "according claim 1," should read --according to claim 1,--;
line 28, "according claim 1," should read --according to claim 1,--;
line 33, "according claim 13," should read --according to claim 13,--;
line 40, "according claim 13," should read --according to claim 13,--;
line 45, "according claim 13," should read --according to claim 13,--;
line 48, "according claim 1," should read --according to claim 1,--;
line 53, "according claim 1," should read --according to claim 1,--; and
line 57, "according claim 1," should read --according to claim 1,--.

Signed and Sealed this
Third Day of February, 2015

Michelle K. Lee
*Deputy Director of the United States Patent and Trademark Office*